US012797088B2

(12) United States Patent
Decasper et al.

(10) Patent No.: US 12,797,088 B2
(45) Date of Patent: Nov. 17, 2026

(54) METHOD FOR CONTROLLING A THERAPEUTIC ULTRASONIC INTERVENTIONAL SYSTEM

(71) Applicant: WaveClear, Inc., Erie, PA (US)

(72) Inventors: Michael Thomas Decasper, Erie, PA (US); Jonathan Masters, Erie, PA (US); Jeffrey Joseph Vaitekunas, Erie, PA (US)

(73) Assignee: WaveClear Inc., Erie, PA (US)

( * ) Notice: Subject to any disclaimer, the term of this patent is extended or adjusted under 35 U.S.C. 154(b) by 97 days.

(21) Appl. No.: 18/278,578

(22) PCT Filed: Feb. 22, 2022

(86) PCT No.: PCT/US2022/017293
§ 371 (c)(1),
(2) Date: Aug. 23, 2023

(87) PCT Pub. No.: WO2022/182648
PCT Pub. Date: Sep. 1, 2022

(65) Prior Publication Data

US 2024/0293132 A1 Sep. 5, 2024

Related U.S. Application Data

(60) Provisional application No. 63/207,340, filed on Feb. 23, 2021.

(51) Int. Cl.
*A61B 17/22* (2006.01)
*A61B 17/00* (2006.01)
*G16H 40/63* (2018.01)

(52) U.S. Cl.
CPC .. *A61B 17/22012* (2013.01); *A61B 17/00234* (2013.01); *G16H 40/63* (2018.01);
(Continued)

(58) Field of Classification Search
CPC ........ A61B 17/00234; A61B 17/22012; A61B 17/320068; A61B 18/00;
(Continued)

(56) References Cited

U.S. PATENT DOCUMENTS

2014/0288465 A1* 9/2014 Akagane ........ A61B 17/320068 601/2
2016/0135883 A1* 5/2016 Herscher ............ A61B 18/1206 606/41
2019/0001154 A1 1/2019 Vortman et al.

FOREIGN PATENT DOCUMENTS

WO WO-2010103469 A1 * 9/2010 ............. A61B 8/461

OTHER PUBLICATIONS

International Search Report and Written Opinion for Application No. PCT/US2022/017293, mailed Jun. 2, 2022, 9 pages.

* cited by examiner

*Primary Examiner* — Mohamed G Gabr
(74) *Attorney, Agent, or Firm* — FBT Gibbons LLP; Vance V. VanDrake, III; Alexander J. Johnson

(57) ABSTRACT

A method for controlling a system, comprising repeatedly monitoring a resonant frequency of a system that includes an ultrasonic transducer, wherein the ultrasonic transducer is powered by an ultrasonic generator and is configured to drive a device at a predetermined level of resonant frequency, and wherein the ultrasonic generator includes a controller configured to monitor operational parameters of the system; detecting a change in resonant frequency based on a comparison of the monitored resonant frequency against a predetermined threshold for resonant frequency; inferring a system-use criteria based on the detected change in the resonant frequency; and adapting system control by using the controller to alter the operational parameters of the system based on the inferred use criteria.

20 Claims, 9 Drawing Sheets

(52) U.S. Cl.
CPC ................. *A61B 2017/0003* (2013.01); *A61B 2017/00123* (2013.01); *A61B 2017/00141* (2013.01); *A61B 2017/00199* (2013.01); *A61B 2017/00238* (2013.01); *A61B 2017/00778* (2013.01); *A61B 2017/00973* (2013.01); *A61B 2017/22017* (2013.01); *A61B 2217/007* (2013.01)

(58) Field of Classification Search
CPC .. A61B 2017/00026; A61B 2017/0003; A61B 2017/00123; A61B 2017/00137; A61B 2017/00141; A61B 2017/00172; A61B 2017/00176; A61B 2017/00199; A61B 2017/00238; A61B 2017/00778; A61B 2017/00973; A61B 2017/22014; A61B 2017/22017; A61B 2017/22039; A61B 2017/320098; A61B 2217/007; A61N 2007/0073; A61N 7/02; A61N 7/022; G16H 40/63
See application file for complete search history.

METHOD FOR CONTROLLING A THERAPEUTIC ULTRASONIC INTERVENTIONAL SYSTEM

BACKGROUND

The disclosed technology relates, in general, to medical devices and, more particularly, to therapeutic ultrasonic surgical and interventional systems and methods.

Ultrasonic instruments can be advantageous because they can be used to cut and/or coagulate organic tissue, dissolve thrombus, disrupt and clear atherosclerosis or perform other therapeutic functions using energy in the form of mechanical vibrations transmitted to a surgical end-effector at ultrasonic frequencies. Ultrasonic vibrations, when transmitted to organic tissue at suitable energy levels and using a suitable end-effector, can be used to cut, dissect, or cauterize tissue, or to break up stones, cross occlusions, dissolve blood clots or perform numerous other procedures. Ultrasonic instruments can be particularly advantageous because of the amount of ultrasonic energy that can be transmitted from the ultrasonic transducer through the waveguide to the surgical end-effector. Such instruments can be suited for use in minimally invasive procedures, such as endoscopic or laparoscopic procedures or interventional radiology procedures, where the end-effector can be passed through a trocar to reach the surgical site or passed through an access port into a patient's vasculature. Flexible waveguides may be used to deliver ultrasonic energy into the vascular system using catheters and standard interventional radiology methodology. The end-effector of a flexible waveguide may deliver the therapeutic energy over an extended length of the waveguide by, for example, using transverse waveguide motion over an active section length of the catheter's end-effector.

Ischemia is a disease state where there is decreased arterial blood flow and oxygenation to the body due to an obstruction or narrowing of the supplying artery. This results in an infarction (cell death) or ischemia of the tissue in the area. In order to treat this disease state, the objective of an intervention therapy is to reestablish blood flow to the area. Currently, there are limited interventional devices to treat this disease state. One approach is to use ultrasound technology to induce cavitation to break-up the fiber structure within a clot in the peripheral vasculature, thereby ablating the clot. This ultrasound treatment is delivered through a wire, which can be called a "waveguide," and oscillates at a frequency that does not harm adjacent healthy tissue.

Many catheter delivery assemblies include single lumen configuration micro access catheter that tracks directly over a guide wire and are extremely flexible and low profile to facilitate access to the extremely tortuous vasculature. Current procedures for treating the vasculature require access across the lesion or site of interest by keeping the guide wire or micro access catheter positioned across the lesion.

For reasons stated above, and for other reasons which will become apparent to those skilled in the art upon reading the present specification, there is a need for systems and methods that provide for therapeutic ultrasonic surgical systems and methods. There is a particular need for dissolving thrombus, disrupting, and clearing atherosclerosis or performing other therapeutic functions using energy in the form of mechanical vibrations transmitted to a surgical end-effector at ultrasonic frequencies. The disclosed technology fulfills these and other needs, and addresses deficiencies in known systems and techniques.

SUMMARY

The following provides a summary of certain example implementations of the disclosed technology. This summary is not an extensive overview and is not intended to identify key or critical aspects or elements of the disclosed technology or to delineate its scope. However, it is to be understood that the use of indefinite articles in the language used to describe and claim the disclosed technology is not intended in any way to limit the described technology. Rather the use of "a" or "an" should be interpreted to mean "at least one" or "one or more".

One implementation of the disclosed technology provides a first method for controlling a system, comprising repeatedly monitoring a resonant frequency of a system that includes an ultrasonic transducer, wherein the ultrasonic transducer is powered by an ultrasonic generator and is configured to drive a device at a predetermined level of resonant frequency, and wherein the ultrasonic generator includes a controller configured to monitor operational parameters of the system; detecting a change in resonant frequency based on a comparison of the monitored resonant frequency against a predetermined threshold for resonant frequency; inferring a system-use criteria based on the detected change in the resonant frequency; and adapting system control by using the controller to alter the operational parameters of the system based on the inferred use criteria.

Adapting system control may comprise at least one of operating the system at a fixed frequency for a predetermined period of time after the system use criteria is inferred; and excluding a frequency range from the operating range of the system. The method may further comprise at least one of monitoring and detecting changes in an operating frequency of the system as it locks onto the transducer and altering the operational parameters in response to detected changes; and monitoring and detecting changes in voltage driving the transducer and altering the operational parameters in response to detected changes.

Another implementation of the disclosed technology provides a second method for controlling a system, comprising repeatedly monitoring a resonant frequency of a system that includes an ultrasonic transducer, wherein the ultrasonic transducer is powered by an ultrasonic generator and is configured to drive a medical device at a predetermined level of resonant frequency, and wherein the ultrasonic generator includes a controller configured to monitor operational parameters of the system; detecting a change in resonant frequency based on a comparison of the monitored resonant frequency against a predetermined threshold for resonant frequency; inferring a system-use criteria based on the detected change in the resonant frequency; and adapting system control by using the controller to alter the operational parameters of the system based on the inferred use criteria.

The method may further comprise using a computer to sense resonance power by a phase-lock-loop detection; or detect ring down frequencies after power is disconnected in one of two or more frequency operating modes. Adapting the system control may comprise at least one of operating the system at a fixed frequency for a predetermined period of time after the system use criteria is inferred; and excluding a frequency range from the operating range of the system. The method may further comprise a second frequency modulation scheme wherein system operating levels are adjusted based on a second frequency modulation criteria.

The method may further comprise measuring and monitoring load impedance over time, wherein an increase or decrease in impedance over time is used to change a set-point of the second frequency modulation scheme. The method may further comprise at least one of monitoring and detecting changes in an operating frequency of the system as it locks onto the transducer and altering the operational parameters in response to detected changes; and monitoring and detecting changes in voltage driving the transducer and altering the operational parameters in response to detected changes. The system may further include a digital signal processor configured to detect an onset of anomalous phase information and adjust the operational parameters accordingly.

Still another implementation of the disclosed technology provides a third method for controlling a system, comprising repeatedly monitoring a resonant frequency of a therapeutic system that includes an ultrasonic transducer, wherein the ultrasonic transducer is powered by an ultrasonic generator and is configured to drive an end-effector at a predetermined level of resonant frequency, and wherein the ultrasonic generator includes a controller configured to monitor operational parameters of the system; detecting a change in resonant frequency based on a comparison of the monitored resonant frequency against a predetermined threshold for resonant frequency; inferring a system-use criteria based on the detected change in the resonant frequency; and adapting system control by using the controller to alter the operational parameters of the system based on the inferred use criteria.

The method may further comprise using a computer to sense resonance power by a phase-lock-loop detection or detect ring down frequencies after power is disconnected in one of two or more frequency operating modes. Adapting system control may comprise at least one of operating the system at a fixed frequency for a predetermined period of time after the system use criteria is inferred and excluding a frequency range from the operating range of the system. The method may further comprise a second frequency modulation scheme wherein system operating levels are adjusted based on a second frequency modulation criteria. The method may include inputting information into the system defining a patient's presentation of clinical criteria. The clinical criteria may include a blood vessel size of a patient in need of treatment for a blood clot, wherein the system alters the second frequency modulation scheme to assure that the entire diameter of the vessel is treated within an operational time limit by adjusting the magnitude of the change of the second operating level adjustments over time. The clinical criteria may also include the occlusion level of a blood vessel in a patient in need of treatment for a blood clot, or the type of blood clot in a patient in need of treatment for a blood clot, wherein the system alters the second frequency modulation scheme to assure that the vessel is optimally treated within an operational time limit by adjusting the magnitude of the change of the second operating level adjustments over time.

The method may further comprise measuring and monitoring load impedance over time, wherein an increase or decrease in impedance over time is used to change a set-point of the second frequency modulation scheme. The method may further comprise at least one monitoring and detecting changes in an operating frequency of the system as it locks onto the transducer and altering the operational parameters in response to detected changes; and monitoring and detecting changes in voltage driving the transducer and altering the operational parameters in response to detected changes. The system may further include a digital signal processor configured to detect an onset of anomalous phase information and adjust the operational parameters accordingly.

The above summary of the disclosed technology is not intended to describe each embodiment or every implementation of the disclosed technology. Advantages and attainments, together with a more complete understanding of the disclosed technology, will become apparent and appreciated by referring to the following detailed description and claims taken in conjunction with the accompanying drawings.

It should be appreciated that all combinations of the foregoing concepts and additional concepts discussed in greater detail below (provided such concepts are not mutually inconsistent) are contemplated as being part of the technology disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed technology and, together with the general description given above and detailed description given below, serve to explain the principles of the disclosed subject matter, and wherein.

DETAILED DESCRIPTION

Figure 1:
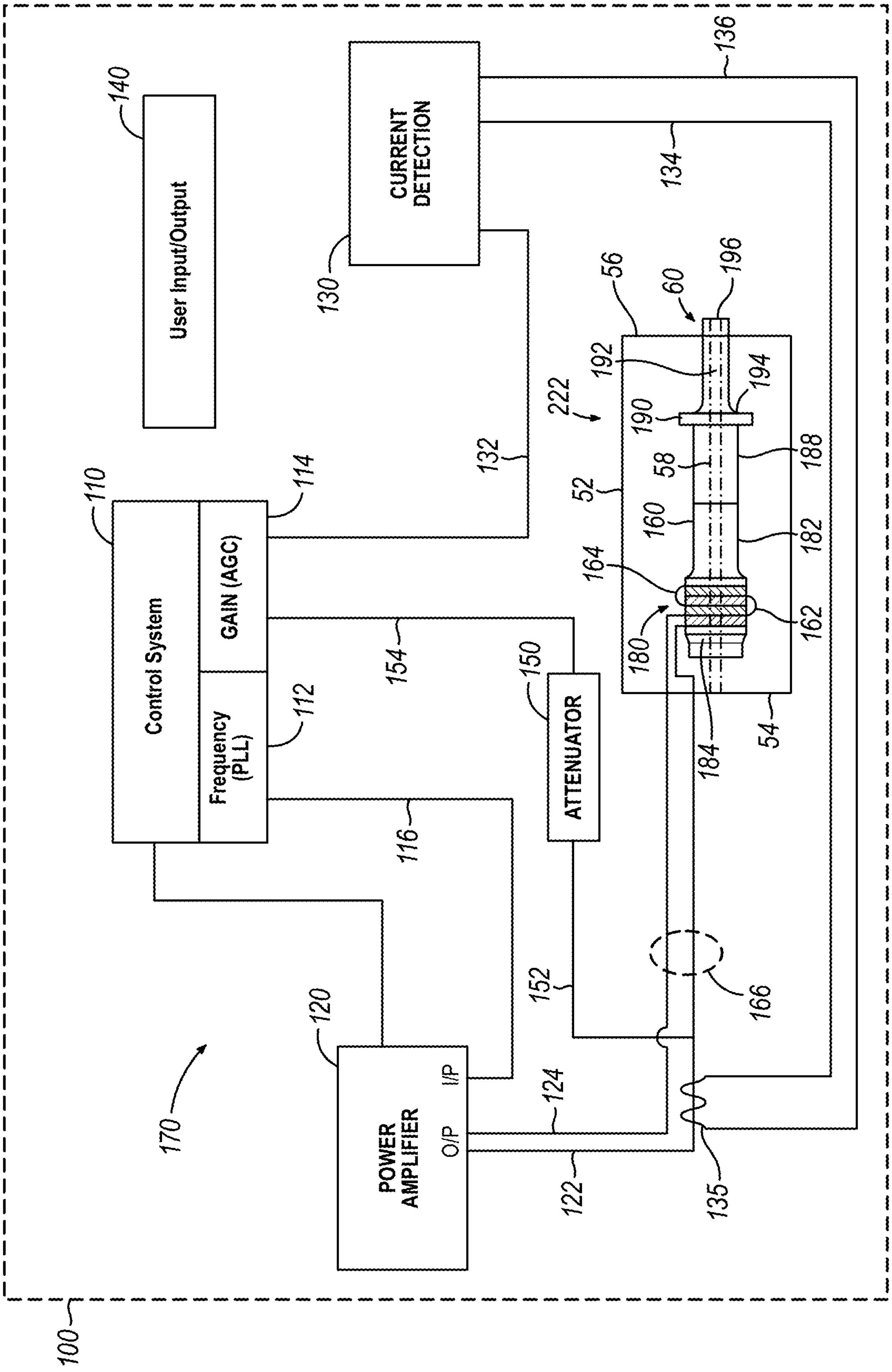
FIG. 1 is a diagrammatic view of an ultrasonic system and a plan view of a sandwich-type ultrasonic transducer according to one embodiment.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed technology. Accordingly, the following implementations are set forth without any loss of generality to, and without imposing limitations upon, the claimed subject matter.

The disclosed technology relates, in general, to medical devices and, more particularly, to therapeutic ultrasonic surgical and interventional systems and methods.

Methods and devices employing ultrasonic energy to dissolve thrombus, disrupt and clear atherosclerosis or performing other therapeutic functions using energy in the form of mechanical vibrations transmitted to a surgical end-effector at ultrasonic frequencies in accordance with the disclosed technology may incorporate one or more of the features, structures, methods, or combinations thereof described herein below. For example, therapeutic ultrasonic medical devices may be implemented to include one or more of the features and/or processes described below. It is intended that such a device or method need not include all of the features and functions described herein but may be implemented to include one or more features and functions that, alone or in combination, provide for unique structures and/or functionality.

The examples discussed herein are examples only and are provided to assist in the explanation of the apparatuses, devices, systems, and methods described herein. None of the features or components shown in the drawings or discussed below should be taken as required for any specific implementation of any of these the apparatuses, devices, systems, or methods unless specifically designated as such. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Ultrasonic instruments in accordance with embodiments described herein can include both hollow core and solid core instruments and can be used for the safe and effective treatment of many medical conditions. Solid core ultrasonic instruments contain solid ultrasonic waveguides that can deliver energy from a transducer to an end-effector that can be used to perform a function such as, for example, dissolving thrombus, removing atherosclerosis, cutting, or coagulating tissue, breaking up hard materials, crossing occlusions, or other surgical procedures. Solid, but flexible, wires can be used as waveguides to deliver ultrasonic energy. Hollow core ultrasonic instruments can contain ultrasonic waveguides that can deliver energy from a transducer to an end-effector that can be used to perform a function such as, for example, cutting or coagulating tissue, breaking up hard materials, crossing occlusions, and other surgical procedures, where the waveguides can have one or more channels that can, for example, be used to deliver fluids or aspirate during procedures utilizing ultrasonic energy. For example, a phaco-emulsifier can have a hollow needle-like end-effector that can aspirate pieces of cataract tissue as the device breaks up a cataract.

In an example embodiment, ultrasonic vibration can be induced in the surgical end-effector by electrically exciting a transducer that can be constructed from one or more piezoelectric or magneto-strictive elements in an instrument hand piece. Vibrations generated by the transducer can be transmitted to a surgical end-effector by way of an ultrasonic waveguide extending from the transducer to the end-effector.

Sandwich-type ultrasonic transducers, such as Langevin transducers, can be used to produce high velocity ultrasonic motion. For example, a sandwich or stack of piezoelectric material positioned between metal plates can be used to generate high intensity ultrasound. Such sandwich transducers can utilize a bolted stack transducer tuned to a resonant frequency and designed to an integer number of half-wavelengths of the resonant frequency.

In an example embodiment, high-intensity ultrasonic transducers of the composite or sandwich type can include front and rear mass members that can include alternating annular piezoelectric elements that can include electrodes stacked there between. Such high-intensity transducers can be pre-stressed and can employ a compression bolt that can extend axially through the stack to place a static bias of about one-half or more of the compressive force that the piezoelectric transducers can tolerate. When the transducers operate, they can be configured or designed to remain in compression and can swing, for example, from a minimum compression of nominally zero to a maximum peak of no greater than the maximum compressive strength of the material.

In an example embodiment, a stud can be threadedly engaged with a front-mass, also called a horn, to provide compressive forces to a transducer piezoelectric stack. Threaded studs or crimp couplers at the distal end of the horn can be used for attaching and detaching transmission components to the transducer assembly. Such bolts, crimp couplers and studs can be utilized to maintain acoustic coupling between elements of the sandwich type transducer or any attached acoustic assembly. Coupling can help maintain tuning of the assembly and can allow the assembly to be driven at the transducer resonance, at the waveguide resonance (if different from the transducer resonance) or at any desired frequency. Sandwich- type transducers can be relatively high-Q devices, and during operation can be driven at or near resonance and can be maintained within a relatively narrow frequency range by feedback control methods.

Systems and methods in accordance with embodiments described herein can provide for controlling the output of high-power ultrasonic transducers and may improve performance of associated ultrasonic systems. Example embodiments can improve energy delivery and can control the output of high-power ultrasonic transducers as energy is delivered through flexible waveguides. FIG. 1 illustrates a diagrammatic view of one embodiment of an ultrasonic system

100 in combination with a plan view of a sandwich-type ultrasonic transducer 160. The ultrasonic transducer 160, which can be known as a "Langevin stack", can include a piezoelectric stack 180, a first resonator or back-mass 184, and a second resonator or front-mass 182. The ultrasonic transducer 160 can include an integral number of one-half system wavelengths (hl/2), where n is an integer and lambda is the acoustic wavelength. For example, the ultrasonic transducer 160 illustrated in FIG. 1 can be a full-wave resonator, including two 12 sections, for a total acoustic length of I, which is one full wavelength. The back-mass 184, piezoelectric stack 180, and front-mass 182 can make up one half-wavelength, and a portion 188, a mounting flange 190 and a transmission rod 192 can make up a second half-wavelength. For example, the ultrasonic transducer 160 illustrated in FIG. 1 can include portion 188, mounting flange 190, a velocity transformer 194, and a distal-end 196 that can be part of the second half-wavelength. In an alternate embodiment such components can be contained in a single half-wavelength. Distal-end 196 can be the end-effector or can be attached to a waveguide leading to an end-effector that can be used to deliver ultrasonic energy to an object, such as tissue, plastic, metal or other object or target.

The distal end of back-mass 184 can be connected to the proximal end of stack 180, and the proximal end of front-mass 182 can be connected to the distal end of stack 180. The front-mass 182 and back mass 184 can be fabricated from titanium, aluminum, stainless steel, or any other suitable material such as materials having a high-Quality factor (Q) value. Front-mass 182 and back-mass 184 can have a length determined by a number of variables, including the thickness of the stack 180, the density and modulus of elasticity of materials used for back-mass 184 and front-mass 182, and the resonant frequency of the ultrasonic transducer 160. The front-mass 182 can be tapered inwardly from its proximal end to its distal end to amplify the ultrasonic vibration amplitude as velocity transformer 194, or alternately can have no amplification.

The stack 180 of the ultrasonic transducer 160 can include a piezoelectric section of alternating positive electrodes 162 and negative electrodes 164, with piezoelectric elements alternating between the electrodes 162 and 164. The piezoelectric elements can be fabricated from any suitable material, such as, for example, lead zirconate-titanate, lead meta-niobate, lead titanate, or other piezoelectric crystal material. Each of the positive electrodes 162, negative electrodes 164, and piezoelectric elements can have a bore extending through the center thereof. The positive and negative electrodes 162 and 164 can be electrically coupled to wires 124 and 122, respectively. Wires 124 and 122 can be encased within a cable 166 and can be electrically connectable to a generator 170 of an ultrasonic system 100.

Referring still to FIG. 1, the ultrasonic transducer 160 can convert the electrical signal from the generator 170 into mechanical energy that can result in vibratory motion of the ultrasonic transducer 160, and any attached end-effector, at ultrasonic frequencies. When the ultrasonic transducer 160 is energized, a vibratory motion standing wave can be generated through the ultrasonic transducer 160. The amplitude of the vibratory motion at any point along the ultrasonic transducer 160 can depend on the location along the ultrasonic transducer 160 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength (1/4).

Distal end 196 at the distal end of the ultrasonic transducer 160 can be placed in contact with tissue of the patient to transfer the ultrasonic energy to the tissue. The cells of the tissue in contact with the distal end 196 of the ultrasonic transducer 160 can be affected by the distal end 196. As the distal end 196 engages the tissue, for example, thermal energy or heat can be generated as a result of internal cellular friction within the tissue. The heat can be sufficient to break protein hydrogen bonds, which can cause the highly structured protein (e.g., collagen and muscle protein) to denature or otherwise become less organized. As the proteins are denatured, a sticky coagulum can form to seal or coagulate small blood vessels such as when the coagulum is below 100° C. Deep coagulation of larger blood vessels can result when the effect is prolonged.

The transfer of the ultrasonic energy to the tissue can cause other effects including mechanical tearing, cutting, cavitation, cell disruption, and emulsification. The amount of cutting as well as the degree of coagulation obtained can vary with the vibrational amplitude of the distal end 196, the amount of pressure applied by the user, and the sharpness of the distal-end 196. The distal end 196 of the ultrasonic transducer 160 can focus the vibrational energy onto tissue in contact with the distal end 196 and can intensify and localize thermal and mechanical energy delivery.

Generator 170 can include a control system 110 that can include a frequency control loop 112 and a gain control loop 114 that can provide for automatic frequency tracking and automatic gain control respectively, based on feedback loop as further described herein. An ultrasonic frequency signal 116 can be provided to a power amplifier 120 that can be used to drive the piezoelectric stack 180. The input (I/P) of the power amplifier 120 can amplify the ultrasonic frequency signal 116 before delivering the amplified signal output (O/P) to the piezoelectric stack 180 using wire 124 as a positive designated signal and wire 122 as a negative designated signal. The positive designated signal wire 124 can be coupled to an attenuator 150 by way of a high voltage signal wire 152. The attenuator can reduce the high voltage signal to an attenuated level (1/250, for example) that can be measured by the gain control loop 114, which can be coupled to the attenuator 150 by low voltage signal wire 154. The gain control loop 114 can be connected to a current detection portion 130 by way of a current level signal wire 132. The current detection portion 130 can determine the current being delivered from the power amplifier 120 to the piezoelectric stack 180 using a current sensor 135 connected by wires 134, 136 to the current detection portion 130.

The ultrasonic generator can include a user input/output 140 that can provide function information to a user such as power level, fault information, system status, or other useful information. The user input/output 140 can also provide for user input to the ultrasonic generator 170 such as desired power level or other desired control or use functional information.

Figure 2:
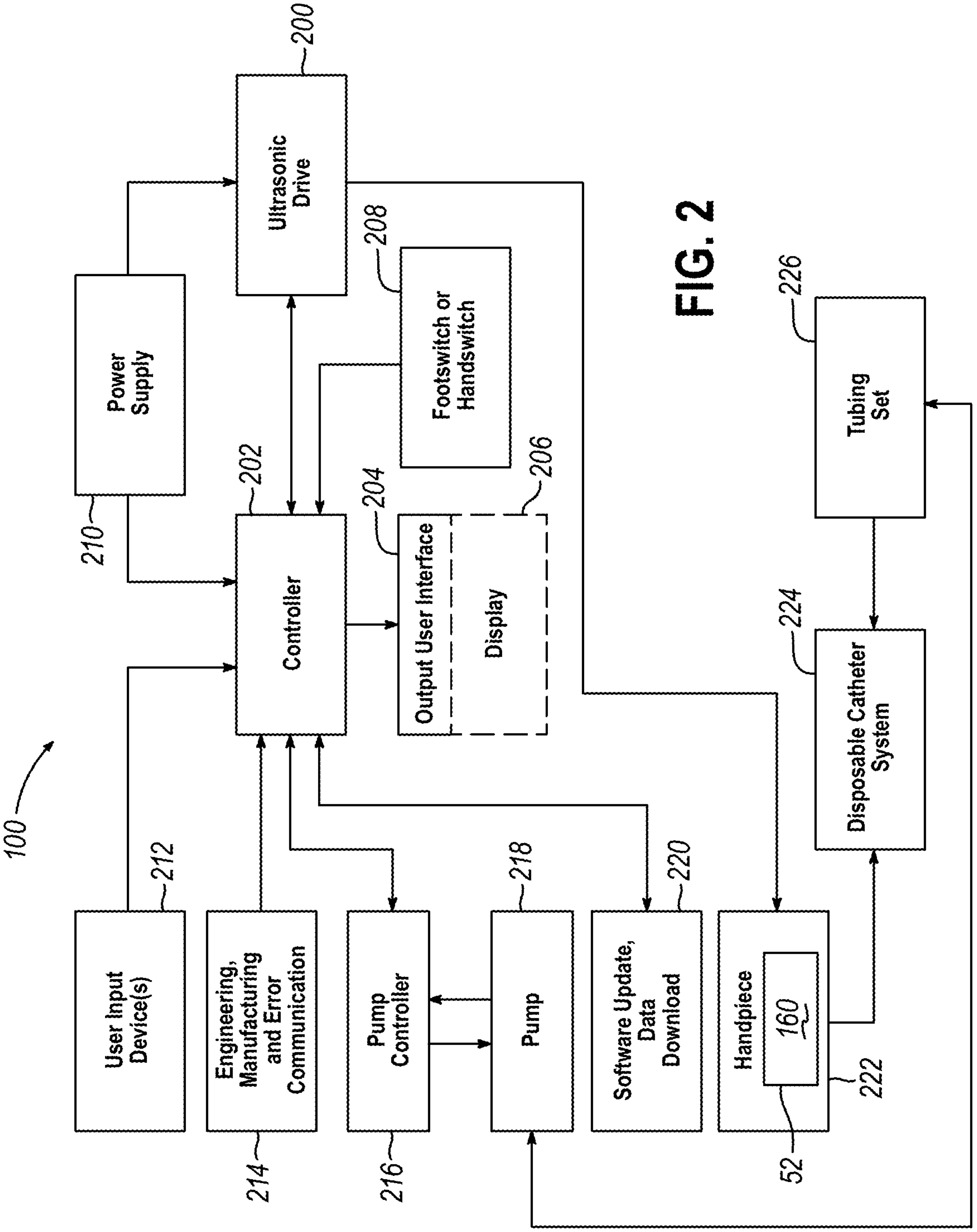
FIG. 2 is a functional block diagram of an ultrasonic system according to one embodiment.

FIG. 2 illustrates a functional block diagram of the ultrasonic system 100 including the generator 170 according to one embodiment. Referring to both FIG. 1 and FIG. 2, when the generator 170 is activated by way of a footswitch or hand switch 208, electrical energy can be continuously applied by the generator 170 to stack 180 of the ultrasonic transducer 160. A phase-lock-loop in a controller 202 of the generator 170 can monitor feedback from the ultrasonic transducer 160 as will be described in more detail herein. The phase-lock-loop can adjust the frequency of the electrical energy sent by the generator 170 to match one or more preselected harmonic frequencies of the ultrasonic transducer 160.

In addition, a second feedback loop, for example the automatic gain control 114, in the control system 110 can maintain and adjust the electrical current supplied to the ultrasonic transducer 160 at one or more preselected levels. These preselected levels can help achieve substantially constant vibrational amplitude at the distal end 196 of the ultrasonic transducer 160 at one or more frequencies of operation and/or one or more modulation schemes. In one embodiment of the disclosed technology, the preselected current level may be increased over time from an initial preselected level, and the current set-point may be increased every preselected time-period of operation of the device. For example, an initial preselected current level may be a current that produces a 15-micrometer peak-to-peak at the distal end of the transducer, and the current level may be increased by 1 micrometer peak-to-peak after every 5 minutes of operation. The phase-lock-loop and current control loop can be non-orthogonal, such that changing one can affect the other.

The electrical signal supplied to the ultrasonic transducer 160 can cause the distal end 196 (FIG. 1) to vibrate longitudinally in the range of, for example, from about 20 KHz to about 500 kHz, from about 20 KHz to about 150 kHz, from about 39 kHz to about 41 kHz or at any other suitable range of frequency of vibration. The amplitude of the acoustic vibrations at the distal end 196 can be controlled, for example, by controlling the amplitude of the electrical signal applied to the stack 180 of the ultrasonic transducer 160 by the generator 170 such as, for example, controlling the applied Voltage level.

As noted above, the footswitch or hand switch 208 of the generator 170 can allow a user to activate the generator 170 so that electrical energy can be continuously supplied to the ultrasonic transducer 160. Continuous supply of energy to the generator 170 can include both continuous wave ultrasonic frequency delivery of energy, and also modulated supply of energy, such as amplitude modulation, frequency modulation, or pulse-width modulation schemes, as well as combinations thereof. In an example embodiment, the footswitch or hand switch 208 can include a foot activated switch that can be detachably coupled or attached to the generator 170 by a cable or cord. In an alternate embodiment, a hand switch can be incorporated in a hand piece assembly 222 and can allow the generator 170 to be activated by a user, for example, by pushing a button (not shown) on the transducer housing.

The generator 170 can also include a power supply 210 that can include a power line for insertion in an electrosurgical unit or conventional electrical outlet. It is contemplated that the generator 170 can also be powered by a direct current (DC) source, such as a battery.

Referring still to FIGS. 1 and 2, the hand piece assembly 222 can include a multi piece housing 52 or outer casing that can be configured to retain the ultrasonic transducer 160 such that the operator can be isolated from the vibrations of the ultrasonic transducer 160. The housing 52 can be substantially cylindrical in shape and can be configured to be held by a user, where any suitable shape and size is contemplated. The housing 52 can be multi-piece, a single component, or a unitary construction.

The housing 52 of the hand piece assembly 222 can be constructed from a durable plastic, such as polycarbonate, polysulfone or PTFE. It is also contemplated that the housing 52 can be made from a variety of materials, such as high impact polystyrene, liquid crystal polymer, polypropylene, or the like.

Referring to FIG. 1, the hand piece assembly 222 can include a proximal end 54, a distal end 56, and can define a centrally disposed axial opening or cavity 58 extending longitudinally therein. The distal end 56 of the hand piece assembly 222 can include an opening 60 that can be configured to allow the ultrasonic transducer 160 of the ultrasonic system 100 to extend therethrough, and the proximal end 54 of the hand piece assembly 222 can be connected to the generator 170 by cable 166.

The mounting flange 190 can be positioned near a node of vibration and can be adjacent a velocity transformer 194, where the velocity transformer 194 can function to amplify the ultrasonic vibratory motion that can be transmitted through the ultrasonic transducer 160 to the distal end 196. In an example embodiment, the velocity transformer 194 can include a solid tapered horn. As ultrasonic energy is transmitted through the velocity transformer 194, the velocity of the acoustic wave can be transmitted through the velocity transformer 194 and can be amplified. It is contemplated that the velocity transformer 194 can be any suitable shape, such as, for example, a stepped horn, a conical horn, an exponential horn, a unitary gain horn, or any other suitable horn design.

The transmission rod 192 can, for example, have a length substantially equal to an integral number of one-half system wavelengths (hl/2). The transmission rod 192 can be constructed from a solid core shaft constructed out of material that can propagate ultrasonic energy efficiently, such as titanium alloy (i.e., Ti-6A1-4V), a nickel-titanium alloy (Nitinol), stainless steel or an aluminum alloy. It is contemplated that the transmission rod 192 can be constructed from any other suitable material, can be hollow or solid core, and can be a flexible wire. The transmission rod 192 can also amplify the mechanical vibrations that can be transmitted through the transmission rod 192 to the distal end 196.

It is also contemplated that the distal end 196 can have a surface treatment (not shown) that can improve the delivery of energy and can provide the desired tissue effect. For example, all or a portion of the distal end 196 can be micro-finished, coated, plated, anodized, etched, grit-blasted, roughened, or scored to enhance efficacy, adjust coagulation in tissue or to reduce adherence of tissue and blood to the end effector. Additionally, the distal end 196 can be rounded, sharpened or shaped such that the energy transmission characteristics can be enhanced for a particular application. For example, the distal end 196 can be an elongated thin wire driven into transverse motion, blade-shaped, hook-shaped, bullet-tipped shaped or ball-shaped.

In an example embodiment, the components of ultrasonic transducer 160 can be acoustically coupled. The distal end of the ultrasonic transducer 160 can be acoustically coupled to the proximal end of an ultrasonic end-effector by, for example, a threaded connection such as a crimp coupling, stud, or threaded bore.

Referring now to FIG. 2, the generator 170 can include a controller 202 that can be integral to the generator 170, a power supply 210, and can include a footswitch or hand switch 208. When activated by the footswitch or hand switch 208, the generator 170 can provide energy to drive the ultrasonic transducer 160 of the ultrasonic system 100 at a predetermined frequency and can drive the distal end 196 (FIG. 1) at one or more predetermined vibrational frequencies or amplitude levels. The generator 170 can drive or excite the ultrasonic transducer 160 at or near any suitable resonant frequency of the ultrasonic transducer 160 or at any desired frequency within a range of the resonant frequency of the ultrasonic transducer 160. For example, the generator 170 can drive or excite the ultrasonic transducer 160 at a fixed frequency, a swept-frequency, or a modulated-frequency within a range of the resonant frequency of the ultrasonic transducer 160. For example, if the of the resonant frequency of the ultrasonic transducer 160 is 40,000 Hertz, the generator 170 may drive the ultrasonic transducer 160 from 39,000 Hertz to 41,000 Hertz cyclically three times every second.

The block diagram of FIG. 2 includes an example of the generator 170 of the ultrasonic system 100. The generator 170 can include a controller 202, where the controller 202 can be a programmed microprocessor which can, for example, be a MOTOROLA model number 68HC11. The controller 202 can be programmed to monitor appropriate power parameters and vibratory frequency and can provide an appropriate power level in various operating modes.

In general, it will be apparent to one of ordinary skill in the art that at least some of the embodiments described herein can be implemented in many different embodiments of software, firmware, and/or hardware. The software and firmware code can be executed by a processor, controller, or any other similar computing device. The software code or specialized control hardware that can be used to implement embodiments is not limiting. For example, embodiments described herein can be implemented in computer software using any suitable computer software language type, using, for example, conventional or object-oriented techniques. Such software can be stored on any type of suitable computer-readable medium or media, such as, for example, a magnetic or optical storage medium. The operation and behavior of the embodiments can be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes described herein can be executed by programmable equipment, such as computers or computer systems and/or processors. Software that can cause programmable equipment to execute processes can be stored in any storage device, such as, for example, a computer system (nonvolatile) memory, an optical disk, magnetic tape, or magnetic disk. Furthermore, at least some of the processes can be programmed when the computer system or controller is manufactured or stored on various types of computer-readable media.

It can also be appreciated that certain portions of the processes described herein can be performed using instructions stored on a computer-readable medium or media that direct a computer system to perform the process steps. A computer-readable medium can include, for example, memory devices such as diskettes, compact discs (CDs), digital versatile discs (DVDs), optical disk drives, or hard disk drives. A computer-readable medium can also include memory storage that is physical, virtual, permanent, temporary, semi-permanent, and/or semi-temporary.

A "controller," "computer," "computer system," "host," "server," or "processor" can be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein can include memory for storing certain software modules used in obtaining, processing, and communicating information. It can be appreciated that such memory can be internal or external with respect to operation of the disclosed embodiments. The memory can also include any means for storing software, including a hard disk, an optical disk, floppy disk, ROM (read only memory), RAM (random access memory), PROM (programmable ROM), EEPROM (electrically erasable PROM) and/or other computer-readable media. Non-transitory computer-readable media, as used herein, comprises all computer-readable media except for a transitory, propagating signals.

Manually operable controls can be provided as user input devices 212 for the purpose of, for example, enabling an operator to adjust the power level to be applied to the transducer assembly when operating. In one embodiment, simultaneous cutting and small vessel coagulation of a predetermined level can be obtained whenever the distal end 196 is in contact with tissue. It is also contemplated that controls can be voice activated, wirelessly transmitted signals, touchscreens, or other input/output devices.

The user input devices 212 may include, without limitation, keyboard entry, writing from pen, stylus, finger, or the like, with a computer mouse, or other forms of input (voice recognition, etc.). The user input devices 212 can include a tablet, desktop, phone, board, or paper. In one embodiment, the user may interact with the ultrasonic system 100 by writing with a smart pen on normal paper, modified paper, or a hard flat surface of their preference. In this embodiment, the user may receive real-time feedback, or at least near real-time feedback, or may synchronize with a controller 202 at a later date. The ultrasonic system 100 can include a personal computer or one or multiple computers in a server-type system.

The generator 170 can include an ultrasonic drive 200 which can be coupled to the ultrasonic transducer 160 through a matching network. In operation, the ultrasonic drive 200 can supply electrical energy to the ultrasonic transducer 160 by way of a matching network (not shown) and an isolation transformer (not shown). Frequency control for generating output signals from the generator 170, corresponding to a resonant frequency of the ultrasonic transducer 160 (carried by the handpiece assembly 222), can be produced through the use of a phase-lock-loop 112 (FIG. 1) that can include a phase detector (shown in FIG. 5, phase-detector 722) and oscillator (shown in FIG. 5, VCO 730). The phase detector can compare the phase of the output driving current and voltage signals with an error signal obtained from an error amplifier (as described below in FIG. 5) used to control the voltage-controlled oscillator to produce the desired output frequency.

The computer or controller 202 can be software updatable using a software update and data download capability 220. The software update, data download capability 220 can be used to program the controller 202 at the time of manufacture, or as software updates are available. It is also contemplated that an engineering, manufacturing, and error communications system 214 can log errors or operational information that can be transmitted and/or stored for tracking usage, tracking hours of run-time, tracking error rates, tracking malfunctions, or providing other data for engineering, manufacturing, or business purposes. An output user interface 204 can be provided that can optionally include a display 206. The display 206 can also include a user input device 212, such as a touch-screen display.

The hand piece assembly 222 can be used to drive the distal end 196 (FIG. 1), which can be at the end of an elongated catheter, for example. A disposable catheter system 224 can be removably connectable to the hand piece assembly 222 and can drive the distal end 196 within the vascular system. The ultrasonic system 100 can include a pump 218, a pump controller 216, and a tubing set 226 and can provide controlled flow of fluid within the disposable catheter system 224 for cooling or lubrication purposes or for the delivery of physician-specified fluids.

Figure 3:
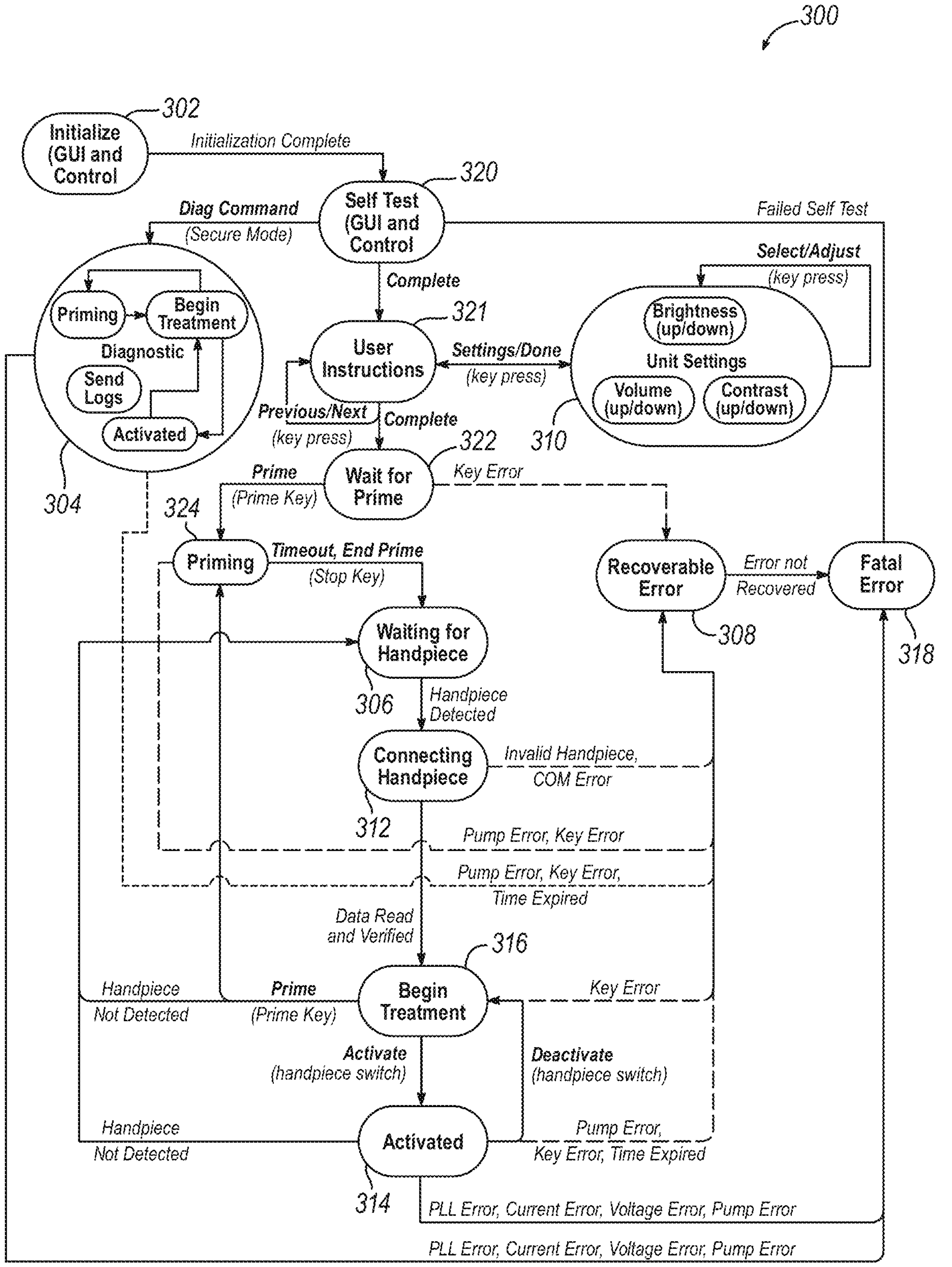
FIG. 3 is a flowchart of a control scheme for an ultrasonic system according to one embodiment.

FIG. 3 is a flowchart of a control scheme 300 for an ultrasonic system in accordance with one embodiment. An initialization step 302 can be used, for example, to power up the components in the generator in a particular order. For example, the controller (e.g., controller 202) can be powered first such that software has time to load and take control of adjustable parameters before power is provided to the power amplifier (e.g., power amplifier 120). A self-test step 320 can be completed, for example, to check that the software was loaded successfully and is functioning, and to make sure that the appropriate power is applied to the appropriate components. A user instruction step 321 can be used to provide user instructions such as, for example, instructing the user how to assemble a device, how to attach tubing and/or fluid containers, how to incorporate pharmaceuticals, or other useful instructions. In response to a key press if a keypad is provided, in response to completion of the instruction step 321, or other desirable initiation, a select/adjust step 310 can optionally be provided to, for example, adjust brightness of a display, adjust volume of a buzzer or speaker, adjust contrast, or other useful selection or adjustment.

When the optional user instruction step 321 or self-test step 320 is completed, a wait state 322 can be entered if some user action is required to continue operation. A recoverable error state 308 can be entered if, for example, a timeout occurs, a software error is detected, a user error is detected, or other recoverable error occurs. If a fatal error 318 occurs, the ultrasonic system 100 can be shut down, can display an error message, can provide an error tone, or other fatal error action or combination of actions can be performed. In embodiments incorporating fluid pumps, flow detectors, bubble detectors, or other fluid management schemes, a priming step 324 can automatically or manually occur. When priming step 324 is completed the ultrasonic system 100 can enter into a waiting for hand piece step 306.

A connecting hand piece step 312 can be used to detect the connection of a hand piece (e.g., hand piece 222), determine characteristics of an already connected hand piece, adjust settings in the generator 170 to control a particular hand piece, diagnose the condition of a hand piece, or other desirable action. Fatal or non-fatal errors can be detected and can send the ultrasonic system 100 into the recoverable error 308 or fatal error 318 states or can enter into a diagnostic 304 state. (NOTE: Fatal and non-fatal does NOT refer to the patient outcome for a medical device but is understood to be a term of the art for software defining when a process is terminated or when an error occurs, and the process is not terminated.) The diagnostic 304 state can be used to diagnose errors, determine criticality of errors, determine condition of transducers (e.g., transducer 160) or associated end-effectors or waveguides, log errors, or other desirable diagnostic action.

If the ultrasonic system 100 is determined to be in adequate condition to function, a begin treatment step 316 can be performed, where ultrasonic energy can be delivered. Fatal or non-fatal errors can be detected and send the ultrasonic system 100 into the recoverable error 308 or fatal error 318 states, or can enter into a diagnostic 304 state, where energy can be turned off or left on depending on the type of error that occurs. Errors can be indicated to the user or logged in an error log as determined by the controller (e.g., controller 202). As the ultrasonic system 100 is activated 314, continuous or occasional monitoring of parameters and errors can occur, and appropriate actions can be implemented. For example, the ultrasonic system 100 can be providing energy even though the phased-lock-loop is not locked onto the operating frequency, while the diagnostic step 304 attempts to regain lock. After, for example, ten attempts to lock onto the transducer resonant frequency, the diagnostic step 304 can send the ultrasonic system 100 into the fatal error 318 mode, where energy delivery can be interrupted.

Figure 4:
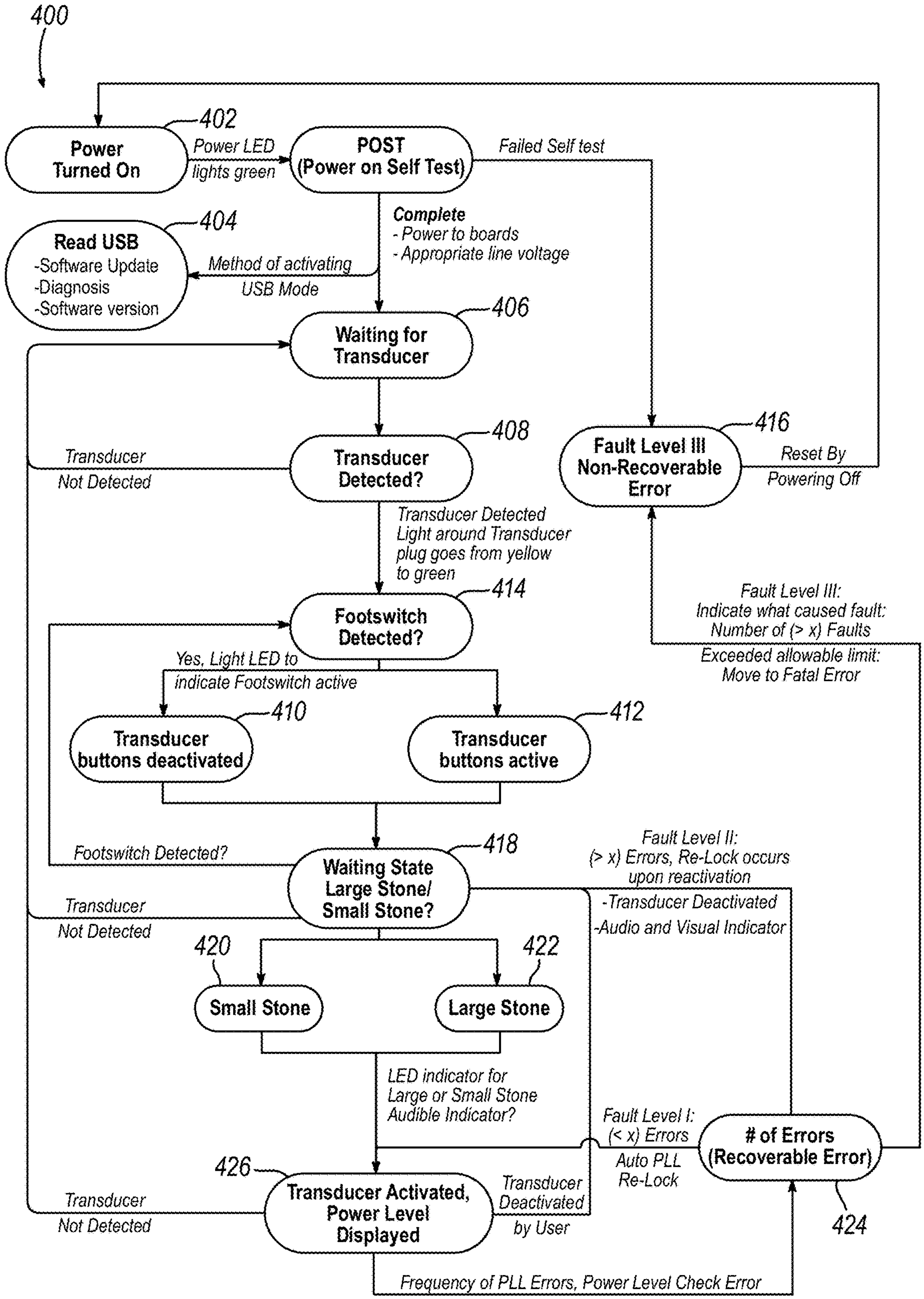
FIG. 4 is a flowchart of a control scheme for an ultrasonic system according to an alternate embodiment.

FIG. 4 is a flowchart of one embodiment of a control scheme 400 for an ultrasonic system 100. In the example control scheme 400 illustrated in FIG. 4, the power turned on step 402 can occur from the push of an on/off switch by a user. A power-on self-test 403 can be performed. If, for example, a dongle (not shown) is attached to a USB port (not shown) on the ultrasonic system 100, a read USB step 404 can be performed to, for example, perform a software update, perform a diagnostic program located on the USB dongle, identify a software version, download an error log, or other desirable input or output using the USB connection. A wait state 406 can be maintained until/unless a transducer (e.g., transducer 160) is connected to the ultrasonic system 100. A transducer connected state 408 can initiate a feedback to the user, such as, for example, where a light (not shown) around the transducer plug lights up or changes color. If a footswitch (e.g., footswitch 208) is available and desired, a footswitch detected state 414 can initiate changes to the system such as, for example, deactivating transducer buttons 410 if transducer switches are available. If no footswitch is connected, a transducer buttons active step 412 can test for button connections, can enable, or disable system features, or can provide for other desired actions. A wait step 418 can include waiting for button or footswitch actuation, watching for errors, or performing other system checks and/or adjustments. Upon actuation by a user, a first operating mode 420 or a second operating mode 422 can be entered. The first operating mode 420 can be, for example, operating the ultrasonic system 100 in a small stone mode for an ultrasonic lithotripsy procedure, operating the ultrasonic system 100 in a first frequency mode for an ultrasonic blood clot dissolving procedure, operating the ultrasonic system 100 in a dual-frequency mode for an ultrasonic lithotripsy procedure, or other desirable operating mode. The second operating mode 422 can be, for example, operating the ultrasonic system 100 in large stone mode for an ultrasonic lithotripsy procedure, operating the ultrasonic system 100 in a second frequency mode for an ultrasonic blood clot dissolving procedure, toggling the system between multiple operating modes, or other desirable actions. System output functional information can be provided to the user as output user interface 204 output (FIG. 2), for example, at output step 426. A transducer-activated indication light (not shown) can light up on the front panel of ultrasonic system 100, a power-level display can display output power, a tone can indicate energy delivery, or other desirable system functions can occur. A number of errors 424 can be recorded, and upon exceeding a predetermined number of errors, a non-recoverable error state 416 can be entered, where the system can be shut down and the user can be forced to cycle the power to attempt to use the system again. Upon re start, the ultrasonic system 100 can use a log of errors to perform additional diagnostics or to display particular information to the user, such as, for example, informing the user to return the system for repair.

Figure 5:
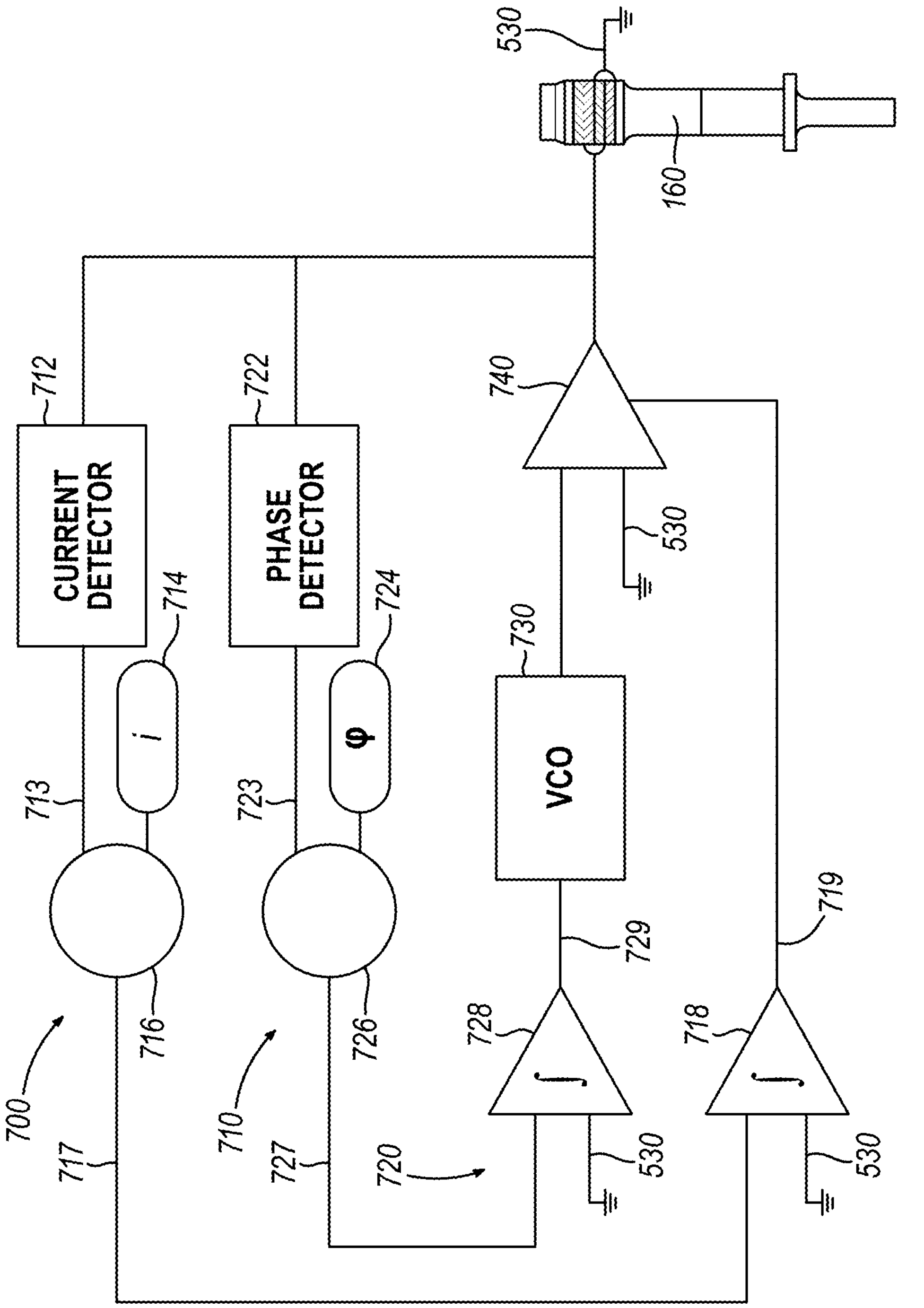
FIG. 5 is a diagrammatic view of an ultrasonic system and a plan view of a sandwich-type transducer according to an alternate embodiment, where the ultrasonic system is shown controlling the transducer at while adjusting amplitudes in accordance with embodiments of the disclosed technology.

FIG. 5 depicts an example embodiment of a control system 700 that can be used for controlling the transducer 160 at multiple frequencies. The generator 170 (FIG. 1) can include a phase detector 722 that can determine a current system phase 723. An error amplifier 726 can compare the current system phase 723 with a desired phase set-point 724 and can provide a phase error signal 727 to a cascade compensator, such as a loop cascade compensator 728, where the loop cascade compensator 728 can be referenced to the common ground 530. The loop cascade compensator 728 can provide a desired operating frequency signal 729 to a voltage-controlled oscillator 730, (designated VCO) which can drive a power amplifier 740 and can determine the frequency of the output signal from the power amplifier 740, but not the amplitude of the output signal from the power amplifier 740.

The generator 170 can include a current detector 712 that can determine a system amplitude 713 if the transducer 160 is run near series-resonance where current is proportional to amplitude. An error amplifier 716 can compare the current system amplitude 713 with a desired amplitude set point 714 and can provide an amplitude error signal 717 to an integrator 718, where the integrator 718 can be referenced to the common ground 530. The integrator 718 can provide a desired operating amplitude signal 719 to the power amplifier 740 and can determine the amplitude of the output signal from the power amplifier 740, but not the frequency of the output signal from the power amplifier 740. Amplitude modulation of the power amplifier 740 can be controlled by adjusting the rails of a power supply providing power to an H-bridge or other amplifier topology in response to the desired operating amplitude signal 719.

Typically amplitude modulation is designed in a system to modulate the output amplitude of the device at a predetermined pulse-repetition Frequency (PRF) and a predetermined duty-cycle. For example, a first modulation scheme may include a PRF of 10 Hertz and a duty-cycle of 50%, corresponding to an amplitude modulation scheme where the system would drive a transducer for 50 milliseconds at a first operating level, and then 50 milliseconds at a second operating level, and repeat that cycle 10 times every second.

Some embodiments of the disclosed technology include a second amplitude modulation scheme, where, for example, one or both of the first and second operating levels are adjusted based on a second-modulation criteria. For example, one second-modulation criteria would be to continuously increase the amplitude set-point as the operator runs the device. If, for example, the expected use time of the device by the operator was 30 minutes, every minute of operation the system may increase the operating amplitude 5% for one or both of the first and second operating levels.

In embodiments of the disclosed technology, one modulation scheme occurs in the Hertz timeframe, e.g., numbers of cycles per second, and the second-modulation scheme occurs at least an order of magnitude longer timeframe, e.g., seconds, or even two orders of magnitude tens of seconds to hundreds of seconds between level changes.

In an example embodiment, an operator may provide information into the system defining the patient's presentation of clinical issues. In one embodiment, for example, the doctor may input the vessel size of a patient who has a blood clot that needs to be treated. The system may then alter the second modulation scheme to assure that the entire diameter of the vessel is treated within the operation time limit by adjusting the magnitude of the change of the second operating level adjustments over time.

In another example embodiment, the doctor may input the occlusion level of the vessel or the type of clot of a patient who has a blood clot that needs to be treated. The system may then alter the second modulation scheme to assure that the vessel is optimally treated within the operation time limit by adjusting the magnitude of the change of the second operating level adjustments over time.

In one embodiment, the system may measure the load impedance and monitor it over time. An increase or decrease in impedance over time may be used to change the set-point of the second modulation scheme. For example, if the measured impedance drops a predetermined percentage over time, the first and second operating levels of the first modulation scheme may be reduced a predetermined amount, or an amount proportional to the percent decrease of the measured impedance, for example.

In another embodiment, the Voltage may be monitored that is driving the transducer. If the Voltage drops a predetermined percentage over time, the first and second operating levels of the first modulation scheme may be reduced by a predetermined amount, or an amount proportional to the percent decrease of the measured impedance, for example.

In another embodiment, the system may monitor the operating frequency of the system as it is locked onto a transducer. If a change of frequency greater than a predetermined amount is detected within a predetermine timeframe, the first and second operating levels of the first modulation scheme may be adjusted a predetermined amount, or an amount proportional to the percent change of the measured lock-frequency, for example.

Referring now to FIGS. 1-5 and 14, the control system 110, which can have both instantaneous current and Voltage signals, can be capable of determining Voltage information, current information, and phase information between Voltage and current. The ultrasonic system 100 (FIG. 1), using the edge detection circuitry available in a Digital Signal Processor (DSP), for example, can implement control algorithms in accordance with the disclosed technology. The DSP can detect the phase of the instantaneous current and instantaneous voltage and can then determine the phase angle between current and voltage at any instant by comparing the time stamps of detected edges of current and voltage as one skilled in the art could appreciate. The DSP can be a supervisor of an analog phase-lock-loop and allow the analog phase-lock-loop to run the system while constantly monitoring the system phase. Alternately, the DSP may be programmed to perform the function of a phase-locked-loop. The system phase is necessarily delayed by averaging and filtering by the separate phase detector of the analog phase-lock-loop.

One advantage of the DSP supervisor is that it can detect the onset of anomalous phase information very fast relative to the analog control system time constant. For example, the DSP can calculate the rate of change of phase between Voltage and Current. When the DSP detects the anomalous phase response, such as when a rate of change of phase exceeds a predetermined threshold, it can freeze or adjust the operation of the analog control loop until the feedback is once again stable.

The system can apply electro-mechanical (ultrasonic) energy for a period of time in the order of an inertial ring up/down time constant of a resonant electro-mechanical (ultrasonic) assembly at one of a plurality of resonances of the assembly, after which energy at one of the other resonances can be applied for a similar time constant. A sum of the vibration due to applied energy, and the energy of the prior vibrational mode at the prior resonance still excited due to inertia can result in a Fourier composite vibrational mode. This composite mode can modulate at the aforementioned time constant/period.

The system can include, for example, a computing system to sense resonance by either a phase-lock-loop detection, or by detecting ring down frequencies after power is disconnected in one of two or more frequency operating modes.

Example systems can utilize a combination of the two methods to start at a frequency slightly below the last frequency detected on ring down for phase-lock-loop capture for maximum capture/lock speed in switching back and forth between operating frequencies. (Also high to low if parallel resonance is used instead of series resonance, starting above the last frequency detected.)

Figure 6:
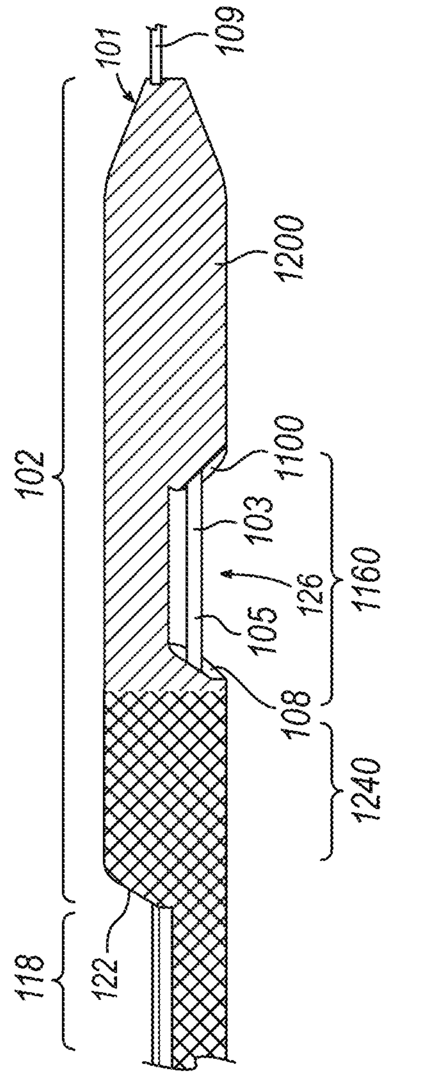
FIG. 6 is a side perspective view of an ultrasound energy delivery assembly in accordance with one embodiment of the disclosed technology.

FIG. 6 shows an ultrasound energy delivery assembly 1000 for thrombectomy, including a monorail rapid exchange micro-access catheter that may be driven by the ultrasonic system 100 described above with respect to FIGS. 1-5. The micro-access catheter 101 can be used for any application with extreme tortuosity that requires a highly flexible, dual-lumen catheter segment. The assembly 1000 also includes a waveguide 103, which has an active zone 105 and an enlarged distal tip 107. The active zone 105 is configured to deliver ultrasound energy in a radial direction. The assembly 1000 is mounted on a standard guide wire 109 when in use.

The micro-access catheter 101 has two lumens that are formed in a single extrusion, a guide wire lumen 104 and a waveguide lumen 106. The guide wire lumen 104 is configured to contain a standard guide wire 109. The waveguide lumen 106 is skived away or closed off using heat and heat shrinkable tubing that is subsequently trimmed, with skives 108, 1100 at the proximal and distal ends of the active zone window 1600 to allow the active zone 105 of waveguide 103 to allow ultrasound treatment energy to access the lesion site.

Figure 7:
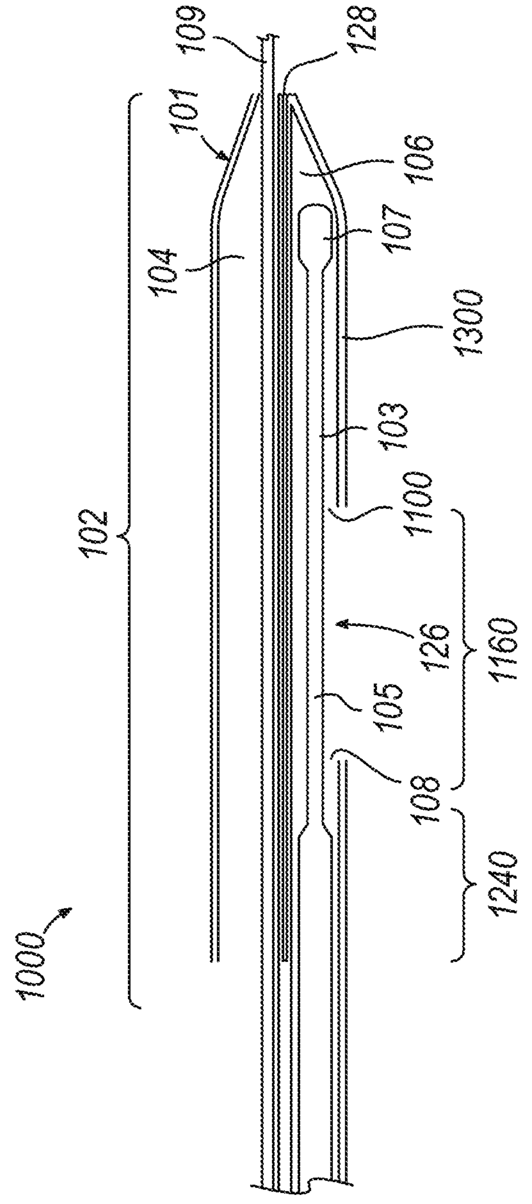
FIG. 7 is a midline longitudinal cross-sectional view of the ultrasound energy delivery assembly in FIG. 6.
Figure 8:
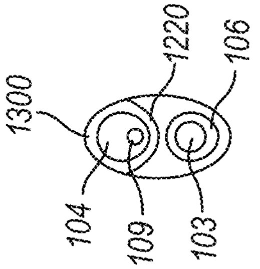
FIGS. 8 and 9 are detailed cross sectional views through the lines 3-3 and 4-4 in FIG. 7, respectively.
Figure 9:
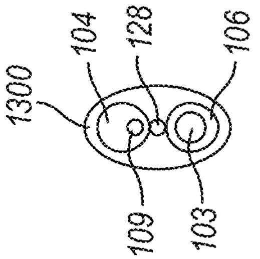

As shown in FIGS. 7-9, the distal dual lumen or "monorail" segment 102 of the micro-access catheter 101 incorporates a single extrusion with dual lumens 104, 106. This dual lumen configuration allows the micro-access catheter 101 to be threaded onto a guide wire 109 and delivered to a target site, leaving the waveguide lumen 106 available to carry a waveguide 103.

Figure 10:
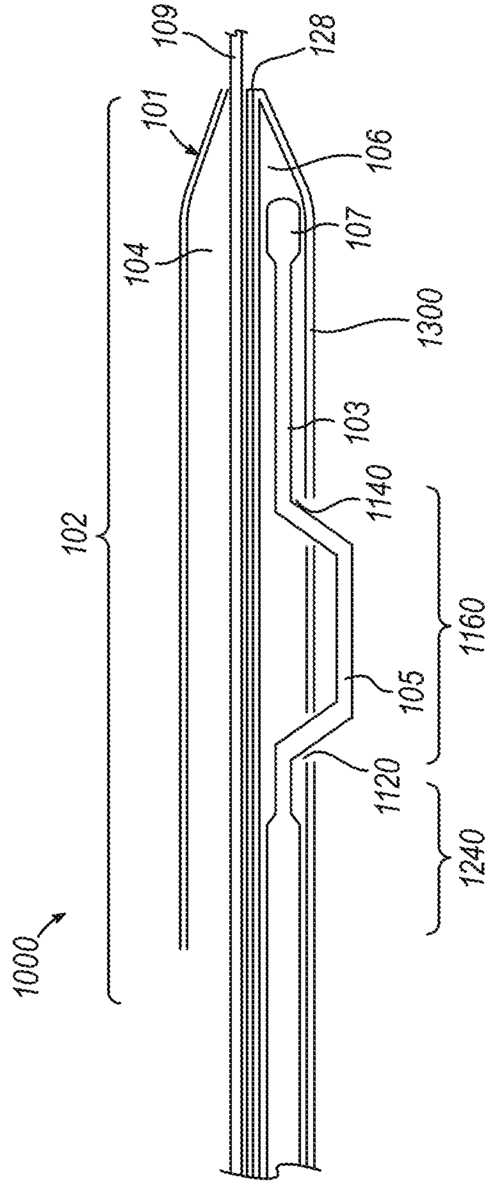
FIG. 10 is a midline longitudinal cross-sectional view of an ultrasound energy delivery assembly in accordance with another embodiment of the disclosed technology.
Figure 11:
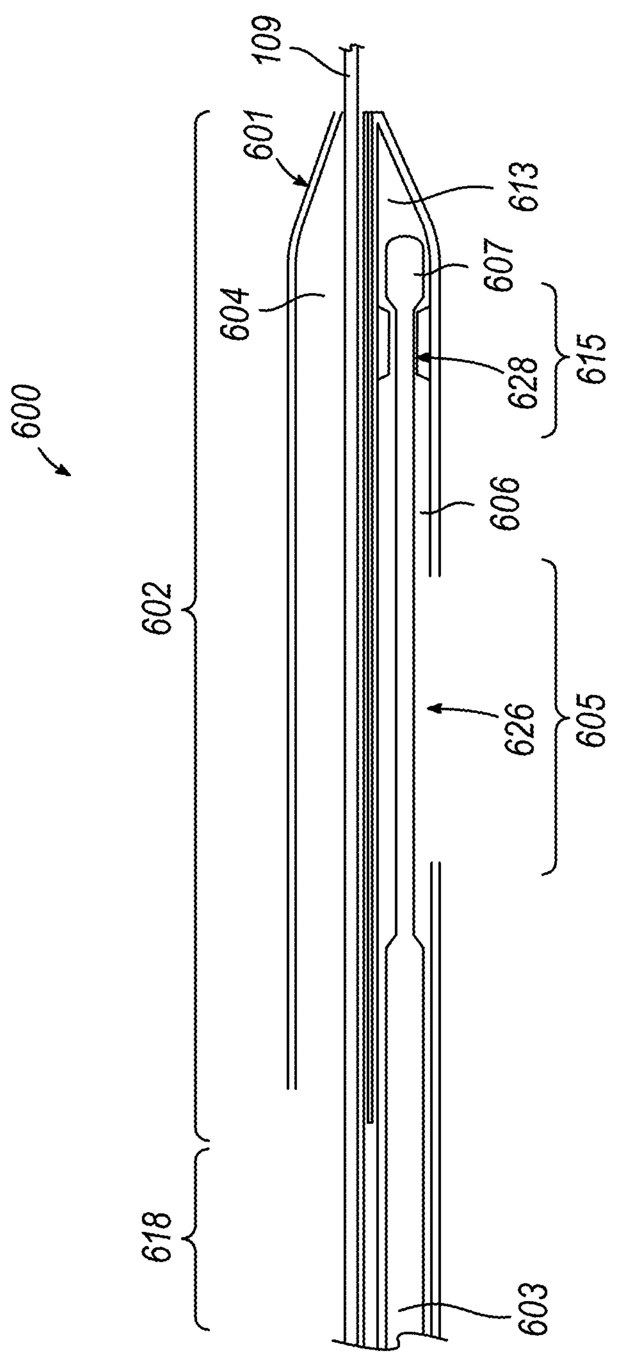
FIG. 11 is a midline longitudinal cross-sectional view of an ultrasound energy delivery assembly.

Another embodiment of the active zone, shown in FIG. 10, includes two skived or cored holes 1120, 1140 with the waveguide lumen 106 between them left open for simplicity, and to retain column strength in the catheter active zone window 1600 to support the thin waveguide active zone 105. The active zone 105 exits and re-enters the catheter 101 through the holes 1120, 1140.

A preferred embodiment utilizes a specialized expanded PTFE (ePTFE) Teflon material that retains the desirable properties of PTFE Teflon such as (but not limited to) low friction coefficient, high tensile strength, and biocompatibility. ePTFE differs from regular PTFE Teflon in that it is expanded during the extrusion process, which renders the material extremely flexible while retaining its desirable properties.

As shown in FIG. 6, a braided, PTFE lined proximal shaft 118 provides adequate column strength and efficiently transfers torque to the distal monorail segment 102, with braid extending onto the monorail segment 102, and braid wires 1200 from one winding direction (clock wise or counter-clock-wise) extend to near the distal tip to transmit torque and kink resistance to the distal tip. A thin-walled tube of Pebax or PTFE Teflon encapsulates the braid and inner extrusions(s) and serves to create a more gradual transition between proximal shaft and monorail segments. An angled lap joint 1220 between proximal shaft and distal monorail segments 118, 102 also helps gradually transition stiffness between the two segments. Extending the braid wires over the joint 1220 and onto the dual-lumen exchange section 1240 (proximal end of monorail segment 102) is another method that gradually transitions stiffness. The active zone window may be reinforced with an axial wire 128.

This micro-access catheter configuration allows a clinician to use currently accepted catheterization procedures, keeping access across the lesion with a standard 0.014" diameter guide wire 109 and exchanging the catheter used to access the lesion for the micro-access catheter 101, or alternatively, using the micro-access catheter 101 to access the lesion.

The polymer outer layer 1300 that encapsulates the braid wires extending over the distal end of the served wires is made from one of the soft grades of Pebax, such as (but not limited to) 3533 or 4033, used with a coating, such as a hydrophilic coating, to reduce frictional drag, or PTFE or ePTFE to eliminate the hydrophilic coating.

In one embodiment, approximate dimensional ranges for the ePTFE monorail segment are as follows: Monorail length 10 cm-40 cm; Monorail OD 0.033"-0.040"; Waveguide lumen ID 0.004"-0.011"; Guide wire lumen ID 0.016"-0.018"; Outer Jacket wall thickness 0.0005"-0.003."

Alternative embodiments can incorporate a vacuum device attached to the delivery catheter. The vacuum device allows the collection and removal of clot fragments. This design feature would also allow the capture of clot through aspiration.

Alternate materials that could suffice for the distal, dual-lumen segment of the neuron/stroke catheter include but are not limited to; PEBAX 3533; EVA or any highly flexible biocompatible polymer that is extrudable in small cross-sections. Further, two separate thin-walled extrusions made from a highly flexible polymer could replace the dual-lumen ePTFE extrusion if they were loosely tied together to maintain flexibility.

The inner layer 304 of the catheter 301 can be constructed with a lubricious polymer such as PTFE. The lubricious inner layer 304 provides for low coefficient of friction as the waveguide 302 moves longitudinally at the proximal section. A (preferably) metal reinforcement layer 306 may be wound over the lubricious inner layer 304 using a material such as (but not limited to) stainless steel or Nitinol wire 308. The reinforcement layer 306 has variable pitch for flexibility at the distal tip and provides maximum column support at the proximal shaft. The proximal reinforcement layer 306 could be composed of multiple layers of coils to provide maximum stiffness. The reinforcement layer 306 terminates distal of the proximal marker 310. The outer layer 312 may be laminated over the reinforcement layer 306. The polymer outer layer 312 can be composed of material of different stiffness to create flexibility at the distal tip and stiffness at the proximal shaft.

Figure 12:
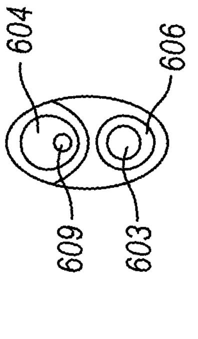
FIGS. 12 and 13 are detailed cross sectional views taken at lines 24-24 and 25-25, respectively, in FIG. 11.
Figure 13:
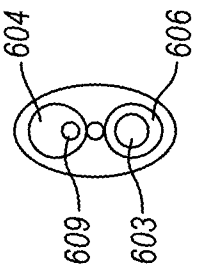

The distal tip may be reinforced with a wire 314 such as Nitinol, as shown in FIG. 12. The wire may be encapsulating between the inner lubricious and outer polymer layer 304, 312 and may be secured in place with the proximal 310 and mid marker band 316. Opposite to the wire, the active zone window 318 may be created by removing the distal shaft material.

A capture tip section 320 may be formed as a part of the catheter 301 using a polymer to form a capture member 328. The capture member 328 extends radially inward from an interior surface of the catheter 301. The capture member 328 allows the passage of the enlarged waveguide distal tip 307 distally under pressure but prevents it from backing out under normal pressures applied during treatment. The distal end 330 of the catheter 301 prevents the waveguide 302 from moving distally. Therefore, once the enlarged waveguide distal tip 307 is moved distal of the capture member

328, the capture member 328 and the distal end 330 of the catheter 301 cooperate to temporarily secure the waveguide 302 in place. In this position, the active zone 305 of the waveguide 302 is positioned adjacent to the active zone window 318 of the catheter 301.

The distal section of the catheter may be sized anywhere from 0-50 cm, and in one embodiment is around 0-10 cm and can be tapered. Just distal to the mid marker band 316 in the distal section is a distal marker band 322 that aids in the visualization of the distal section during treatment. An atraumatic tip can be formed by fusing the polymer tubing at the distal end of the shaft.

A micro-access catheter 101 in accordance with embodiments of the disclosed technology may be driven by an ultrasonic system 100 in accordance with embodiments of the disclosed technology providing an ultrasonic medical device that generates vibration along its longitudinal axis. The ultrasonic vibration is transmitted through an ultrasonic coupler and a series of transformer sections that amplify the ultrasonic vibration. A flexible member is coupled to the distal end of the transformer sections and is thus supplied with a longitudinal vibration by the transformer sections. The flexible member is designed so that it converts the longitudinal vibration into a standing wave that runs along the length of an active zone near the distal end of the flexible member. The standing wave produces a series of transverse nodes and anti-nodes along the length of the active zone of the flexible member. Each of the anti-nodes produces cavitation in fluids in contact with the probe. The cavitation of the fluids causes destruction of adjacent thrombus or calcifications.

In a fluid or fluid containing medium, each of the anti-nodes (positions corresponding to maximum transverse displacement) along the length of the probe cause cavitation of the fluid in a direction perpendicular to the longitudinal axis of the probe. Cavitation is a void or bubble produced by the inability of the fluid to overcome the stresses induced by the motion of the probe. The collapse of the cavitation bubbles in and around cellular (or biological) material produces a shockwave that erodes or fragments the material.

The driver and transformer sections are designed to provide sufficient longitudinal amplitude to support the desired transverse mode amplitude. Typically, the handle and probe assembly are designed to support a longitudinal amplitude which will be sufficient to induce buckling in the flexible member. It should be noted that there is no longitudinal vibration of the most distal tip as this is converted entirely into a transverse vibration through buckling of the thin member at the tip.

The transverse mode probe is much more effective at thrombus removal than are the longitudinal designs of the prior art. One reason for this is because the action of the energy is along most of the length of the exposed flexible member and is not confined to the surface area of the tip of the member. The probes described in the prior art which are only driven in the longitudinal direction only work at the tip. Even with a solid tip, its active area in contact with tissue is much less than the transverse mode tip. Also, the tissue destruction of the transverse mode probes extends up to 1 mm or more circumferentially beyond the probe.

Embodiments of the disclosed technology are directed to methods to detect and respond to tortuosity of the vasculature as the catheter is moved through the anatomy. As a catheter containing an ultrasonic waveguide is advanced or moved through anatomical tortuosity, the ultrasonic waveguide experiences changes in the parameters measurable by the generator system. These changes may be used to adapt the output of the system to compensate for effects due to the tortuosity. For example, a bend of the catheter through tortuosity may cause an ultrasonic reflection in the waveguide that leads to an impedance change in the system, such that the system may try to track the resonance of the reflection and not the resonance of the transducer. The system in accordance with the disclosed technology may be adapted to recognize the effects of tortuosity and compensate the system to improve efficacy.

Figure 14:
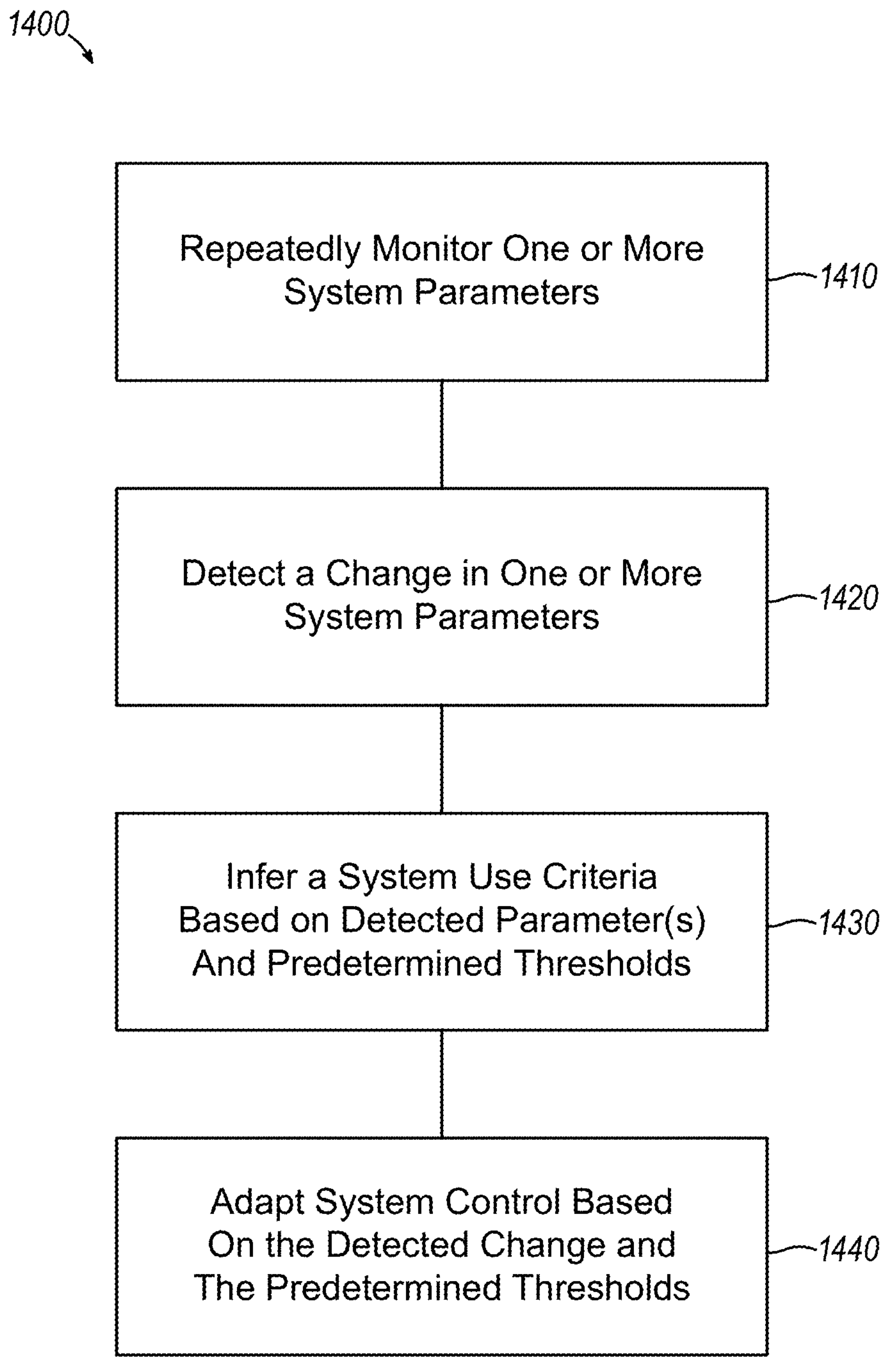
FIG. 14 is a flowchart of a second-modulation scheme of an ultrasonic system operating in accordance with aspects of the disclosed technology.

For example, FIG. 14 is directed to a system control algorithm 1400 configured to adapt and correct the system 100 as the system 100 is used to perform its operations. As system 100 is driving transducer 160, a step 1410 of repeatedly monitoring one or more system parameters may be performed. For example, the system 100 may measure and record a parameter of the system 100 corresponding to the Voltage and current being delivered to the transducer 160. This recorded parameter may be compared in software to a predetermined threshold and the rate of change of the parameter may be compared to a predetermined rate of change as part of a detection step 1420. In one embodiment an inference step 1430 may be performed in software to infer a system use criteria based on the detected parameter or parameters and predetermined thresholds. A step 1440 adapts the system 100 control based on the detected change step 1420 and the inference step 1430.

In one embodiment, the transducer 160 drive frequency may be monitored, and the rate of change of the drive frequency may be detected. It is known that the transducer 160 drive frequency may change by, for example, 150 Hertz reduction in frequency over one minute drive operation as the transducer heats and the resonant frequency drops accordingly. This rate of change corresponds to a system 100 operating characteristic of 150 Hertz per minute. A threshold may be set as, for example, 150 Hertz per 10 seconds as a predetermined threshold that the rate of change of frequency is exceeding the rate of change expected from normal heating during operation. The system 100 may then, for example, infer that a reflection for a tortuous bend in the catheter is occurring and that the actual resonant frequency of the system 100 is locking onto the reflection and not the transducer 160. Based on this inference, the system 100 may correct itself by, for example, temporarily operating at a frequency corresponding to the previously monitored operating frequency from before the detected rate of change of resonant frequency occurred.

In another embodiment, the transducer 160 drive impedance may be monitored, and the rate of change of the drive impedance may be detected. It is known that the transducer 160 drive impedance may change by, for example, 1000 Ohm increase in impedance during operation of the transducer as the catheter clears clot from within a subject, but that a decrease of 200 Ohms is not likely to occur during expected operation unless significant tortuosity is encountered. A threshold may be set as, for example, a 200 Ohm decrease of operating impedance as a predetermined threshold that the change in impedance is exceeding the change expected from normal operation. The system 100 may then, for example, infer that a reflection for a tortuous bend in the catheter is occurring and that the waveguide of the catheter is experiencing a local resonance causing a reduction in impedance. Based on this inference, the system 100 may correct itself by, for example, temporarily operating at a reduced current setpoint thereby reducing system amplitude during the lowered impedance time-period, and then again increasing the current set-point if a subsequent measured impedance increases back within the expected range.

In yet another embodiment, the transducer 160 drive time may be monitored, and the duration of operation of the system may be detected. It is known that the system 100 may operate a transducer 160 for a limited time period of operation. For example, a transducer 160 may be limited to 30 minutes of operation time before the catheter is expired and no longer usable. Step 1410 may monitor catheter run-time. Step 1420 may detect that an amount of time has occurred, such as, for example, a continuous minute of operation time. In step 1430, a threshold may be set as, for example, a predetermined threshold of every incremental minute of operation. The system 100 may then, for example, infer that the active section of the catheter has cleared a range of clot within its reach. Based on this inference, the system 100 may correct itself by, for example, increasing the current set-point of the system, thereby increasing the amplitude of the output of the active zone, which would then provide for an expanded reach of the clot clearing capability of the active zone.

In a further embodiment, the generator 170 may provide for the user to input information into the generator 170 regarding patient presentation, such as, for example, vessel diameter, clot length, clot type, clot age, and other useful patient data. The generator 170 may then adjust predetermined thresholds, ranges and other operating parameters based on the patient presentation information provided by the user that may be used during the inference step 1430 and the adapting step 1440.

It is understood that the components and functionality depicted in the figures and described herein may be implemented in hardware, software, or a combination of hardware and software. It is further understood that the components and functionality depicted as separate or discrete blocks/elements in the figures may be implemented in combination with other components and functionality, and that the depiction of such components and functionality in individual or integral form is for purposes of clarity of explanation, and not of limitation.

Illustrations of method steps, such as, for example, the steps illustrated in FIGS. 3, 4 and 14 show steps sequentially and in a particular order. There is no need to perform the steps in the order illustrated. Departing from the illustrated order for some or all of the steps is contemplated by the inventor and does not depart from the scope of the disclosed technology.

Each feature disclosed in this specification (including any accompanying claims, abstract, and drawings), may be replaced by alternative features having the same, equivalent, or similar purpose, unless expressly stated otherwise. Thus, unless expressly stated otherwise, each feature disclosed is one example only of a generic series of equivalent or similar features.

While preferred embodiments of the disclosed technology have been shown and described herein, it will be obvious to those skilled in the art that such embodiments are provided by way of example only. Numerous variations, changes, and substitutions will be apparent to those skilled in the art without departing from the disclosed technology. Accordingly, it is intended that the disclosed technology be limited only by the scope of the appended claims.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differ from or contradict this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particularly suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about", if or when used throughout this specification describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed technology. Various functions and elements described herein may be partitioned differently from those shown without departing from the scope of the disclosed technology. Generic principles defined herein may be applied to other implementations. Different numbers of a given module or unit may be employed, a different type or types of a given module or unit may be employed, a given module or unit may be added, or a given module or unit may be omitted.

Regarding this disclosure, the term "a plurality of" refers to two or more than two. Unless otherwise clearly defined, orientation or positional relations indicated by terms such as "upper" and "lower" are based on the orientation or positional relations as shown in the figures, only for facilitating description of the disclosed technology and simplifying the description, rather than indicating or implying that the referred devices or elements must be in a particular orientation or constructed or operated in the particular orientation, and therefore they should not be construed as limiting the disclosed technology. The terms "connected", "mounted", "fixed", etc. should be understood in a broad sense. For example, "connected" may be a fixed connection, a detachable connection, or an integral connection; a direct connection, or an indirect connection through an intermediate medium. For an ordinary person skilled in the art, the specific meaning of the above terms in the disclosed technology may be understood according to specific circumstances.

It should be appreciated that all combinations of the foregoing concepts and additional concepts discussed in greater detail herein (provided such concepts are not mutually inconsistent) are contemplated as being part of the disclosed technology. In particular, all combinations of claimed subject matter appearing at the end of this disclosure are contemplated as being part of the technology disclosed herein. While the disclosed technology has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed technology in its broader aspects is not limited to any of the specific details, representative devices, and methods, and/or illustrative examples shown and described. Accordingly, departures may be made from such details without departing from the spirit or scope of the general inventive concept.

What is claimed:

1. A method for controlling a system, comprising:

(a) repeatedly monitoring a resonant frequency of a system that includes an ultrasonic transducer, (i) wherein the ultrasonic transducer is powered by an ultrasonic generator and is configured to drive a device at a predetermined level of resonant frequency, and (ii) wherein the ultrasonic generator includes a controller configured to monitor operational parameters of the system;

(b) detecting a change in resonant frequency based on a comparison of the monitored resonant frequency against a predetermined threshold for resonant frequency;

(c) inferring a system-use criteria based on the detected change in the resonant frequency; and (d) adapting system control by using the controller to alter the operational parameters of the system based on the inferred use criteria, and to exclude a frequency range from an operating range of the system.

2. The method of claim 1, wherein adapting the system control further comprises:

operating the system at a fixed frequency for a predetermined period of time after the system use criteria is inferred.

3. The method of claim 1, further comprising at least one of:

(a) monitoring and detecting changes in an operating frequency of the system as it locks onto the transducer and altering the operational parameters in response to detected changes; and (b) monitoring and detecting changes in voltage driving the transducer and altering the operational parameters in response to detected changes.

4. A method for controlling a system, comprising:

(a) repeatedly monitoring a resonant frequency of a system that includes an ultrasonic transducer, (i) wherein the ultrasonic transducer is powered by an ultrasonic generator and is configured to a drive (a) medical device at a predetermined level of resonant frequency, and (ii) wherein the ultrasonic generator includes a controller configured to monitor operational parameters of the system;

(b) detecting a change in resonant frequency based on a comparison of the monitored resonant frequency against a predetermined threshold for resonant frequency;

(c) inferring a system-use criteria based on the detected change in the resonant frequency; and (d) adapting system control by using the controller to alter the operational parameters of the system based on the inferred use criteria; and to exclude a frequency range from an operating range of the system.

5. The method of claim 4, further comprising using a computer to:

(a) sense resonance power by a phase-lock-loop detection; or (b) detect ring down frequencies after power is disconnected in one of two or more frequency operating modes.

6. The method of claim 4, wherein adapting the system control further comprises:

operating the system at a fixed frequency for a predetermined period of time after the system use criteria is inferred.

7. The method of claim 4, further comprising a second frequency modulation scheme wherein system operating levels are adjusted based on a second frequency modulation criteria.

8. The method of claim 7, further comprising measuring and monitoring load impedance over time, wherein an increase or decrease in impedance over time is used to change a set-point of the second frequency modulation scheme.

9. The method of claim 4, further comprising at least one of:

(a) monitoring and detecting changes in an operating frequency of the system as it locks onto the transducer and altering the operational parameters in response to detected changes; and (b) monitoring and detecting changes in voltage driving the transducer and altering the operational parameters in response to detected changes.

10. The method of claim 4, wherein the system further includes a digital signal processor configured to detect an onset of anomalous phase information and adjust the operational parameters accordingly.

11. A method for controlling a system, comprising:

(a) repeatedly monitoring a resonant frequency of a therapeutic system that includes an ultrasonic transducer, (i) wherein the ultrasonic transducer is powered by an ultrasonic generator and is configured to drive an end-effector at a predetermined level of resonant frequency, and (ii) wherein the ultrasonic generator includes a controller configured to monitor operational parameters of the system;

(b) detecting a change in resonant frequency based on a comparison of the monitored resonant frequency against a predetermined threshold for resonant frequency;

(c) inferring a system-use criteria based on the detected change in the resonant frequency; and (d) adapting system control by using the controller to alter the operational parameters of the system based on the inferred use criteria; and to exclude a frequency range from an operating range of the system.

12. The method of claim 11, further comprising using a computer to:

(a) sense resonance power by a phase-lock-loop detection; or (b) detect ring down frequencies after power is disconnected in one of two or more frequency operating modes.

13. The method of claim 11, wherein adapting the system control further comprises:

operating the system at a fixed frequency for a predetermined period of time after the system use criteria is inferred.

14. The method of claim 11, further comprising a second frequency modulation scheme wherein system operating levels are adjusted based on a second frequency modulation criteria.

15. The method of claim 14, wherein the method includes inputting information into the system defining a patient's presentation of clinical criteria.

16. The method of claim 15, wherein the clinical criteria include a blood vessel size of a patient in need of treatment for a blood clot, and wherein the system alters the second frequency modulation scheme to assure that the entire diameter of the vessel is treated within an operational time limit by adjusting the magnitude of the change of the second operating level adjustments over time.

17. The method of claim 15, wherein the clinical criteria include the occlusion level of a blood vessel in a patient in need of treatment for a blood clot, or the type of blood clot in a patient in need of treatment for a blood clot, and wherein the system alters the second frequency modulation scheme to assure that the vessel is optimally treated within an operational time limit by adjusting the magnitude of the change of the second operating level adjustments over time.

18. The method of claim 14, further comprising measuring and monitoring load impedance over time, wherein an increase or decrease in impedance over time is used to change a set-point of the second frequency modulation scheme.

19. The method of claim 11, further comprising at least one of:

(a) monitoring and detecting changes in an operating frequency of the system as it locks onto the transducer and altering the operational parameters in response to detected changes; and (b) monitoring and detecting changes in voltage driving the transducer and altering the operational parameters in response to detected changes.

20. The method of claim 11, wherein the system further includes a digital signal processor configured to detect an onset of anomalous phase information and adjust the operational parameters accordingly.

* * * * *